(12) United States Patent
Takeuchi

(10) Patent No.: US 9,683,951 B2
(45) Date of Patent: Jun. 20, 2017

(54) SAMPLE HOLDER FOR X-RAY ANALYSIS AND JIG FOR SAMPLE INSTALLATION

(71) Applicant: Hitachi High-Tech Science Corporation, Minato-ku, Tokyo (JP)

(72) Inventor: Toshitada Takeuchi, Tokyo (JP)

(73) Assignee: Hitachi High-Tech Science Corporation, Minato-ku, Tokyo (JP)

( * ) Notice: Subject to any disclaimer, the term of this patent is extended or adjusted under 35 U.S.C. 154(b) by 220 days.

(21) Appl. No.: 14/620,936

(22) Filed: Feb. 12, 2015

(65) Prior Publication Data

US 2015/0226686 A1    Aug. 13, 2015

(30) Foreign Application Priority Data

Feb. 13, 2014   (JP) .................. 2014-025475

(51) Int. Cl.
    *H05G 1/00*       (2006.01)
    *G01N 23/22*      (2006.01)
    *G01N 23/223*     (2006.01)

(52) U.S. Cl.
    CPC ....... *G01N 23/2204* (2013.01); *G01N 23/223* (2013.01)

(58) Field of Classification Search
    CPC .................. G01N 23/2204; G01N 23/223
    USPC ................................ 378/204, 208
    See application file for complete search history.

(56) References Cited

U.S. PATENT DOCUMENTS 4,587,666 A * 5/1986 Torrisi ............... G01N 23/2204
                                                   378/208
4,974,244 A * 11/1990 Torrisi ............... G01N 23/2204
                                                   378/45

FOREIGN PATENT DOCUMENTS

JP          2000-230912 A    8/2000

* cited by examiner

*Primary Examiner* — Courtney Thomas
(74) *Attorney, Agent, or Firm* — Banner & Witcoff, Ltd.

(57) ABSTRACT

A sample holder for X-ray analysis is provided with: a first annular member; a second annular member configured to be inserted and fitted into the first annular member in a state where a first film is sandwiched between the first annular member and the second annular member while the first film is being stretched to cover a lower opening portion of the second annular member; and a third annular member configured to be inserted and fitted into the second annular member in a state where a second film is sandwiched between the second annular member and the third annular member while the second film is being stretched to cover a lower opening portion of the third annular member. The first film and the second film are configured to hold a sample for X-ray analysis by sandwiching the sample between the first film and the second film.

3 Claims, 4 Drawing Sheets

SAMPLE HOLDER FOR X-RAY ANALYSIS AND JIG FOR SAMPLE INSTALLATION

CROSS-REFERENCE TO RELATED APPLICATION

This application claims priority from Japanese Patent Application No. 2014-025475, filed on Feb. 13, 2014, the entire subject matter of which is incorporated herein by reference.

BACKGROUND

1. Technical Field

The present invention relates to a sample holder for X-ray analysis for holding a sample and setting the sample in an X-ray analyzer when performing X-ray analysis of the sample in the X-ray analyzer, and a jig for sample installation which is used in order to set a sample in the sample holder.

2. Description of the Related Art

Conventionally, when performing X-ray analysis of a sample in an X-ray analyzer such as an X-ray fluorescence spectrometer, a holder for holding the sample is used, and the holder is set in the X-ray analyzer and analysis is then performed. For example, in the related art, in order to analyze and measure a minute sample, a container with film is used as a sample holder. That is, the sample is placed on a thin film stretched in the container and measurement is then carried out.

When measuring the sample on the film in this manner, since the sample is minute and lightweight, shifting of the sample sometimes occurs in which a target position for irradiation of the sample with X-rays and an actual irradiation position do not coincide with each other due to machine vibration or the like at the time of the opening and closing of a door of a device or the exchange of the sample. A method of holding a sample by using a cushioning material in order to ameliorate the shifting of a sample is also proposed. However, there is a problem in that there are cases where the quality of a material of the cushioning material affects an X-ray measurement result.

For this reason, a technique of using a dedicated measurement container is proposed. For example, in JP-A-2000-230912, a sample holder for X-ray analysis is proposed which is provided with a bottomed cylindrical main body, one or more rod-like support members which are provided to be erect on a bottom wall of the main body and support samples at the tip surfaces, and a film which covers an opening portion of the main body and supports the samples between itself and the support members. This sample holder for X-ray analysis is used by providing an insertion opening in the upper surface of the inside of a lid of a container which is a dedicated container and inserting the sample from the insertion opening, or inserting a rod with the sample attached to an end.

The following problems remain in the related art described above.

That is, an X-ray intensity depends on the distance between a sample and an X-ray tube. However, in the sample holder of the related art, it may be necessary to set a sample by inserting the sample into the container, and it is difficult to hold the sample always at the optimum distance, and thus there is a problem in that a measurement result is affected. Further, there may be a limit to the size of the sample which is inserted, and thus it may be necessary to process the sample into a size or a shape capable of being inserted from the insertion opening. There may also be problem in that it takes time for the fabrication of the sample and the fabrication of the sample is complicated.

SUMMARY

The present invention has been made in view of the above-described circumstances, and one of objects of the present invention is to provide a sample holder for X-ray analysis which eliminates shifting of a sample, capable of making the distance between the sample and an X-ray tube constant, and capable of dealing with samples of various shapes, and a jig for sample installation which is used when setting a sample in the holder.

According to an exemplary embodiment of the present invention, there is provided a sample holder for X-ray analysis, which is provided with: a first annular member; a second annular member configured to be inserted and fitted into the first annular member in a state where a first film is sandwiched between the first annular member and the second annular member while the first film is being stretched to cover a lower opening portion of the second annular member; and a third annular member configured to be inserted and fitted into the second annular member in a state where a second film is sandwiched between the second annular member and the third annular member while the second film is being stretched to cover a lower opening portion of the third annular member. The first film being stretched to cover the lower opening portion of the second annular member and the second film being stretched to cover the lower opening portion of the third annular member are configured to hold a sample for X-ray analysis by sandwiching the sample between the first film and the second film.

According to another exemplary embodiment of the present invention, there is provided a jig for installing a sample in the sample holder for X-ray analysis according to the exemplary embodiment. The jig is provided with: a plate-shaped jig main body having an installation hole into which a lower portion of at least the first annular member is fitted; and a transparent plate portion provided to cover a lower opening portion of the installation hole. The transparent plate is provided with a mark indicating the center of the installation hole.

BRIEF DESCRIPTION OF THE DRAWINGS

The above and other aspects of the present invention will become more apparent and more readily appreciated from the following description of illustrative embodiments of the present invention taken in conjunction with the attached drawings, in which.

DETAILED DESCRIPTION

Figure 1:
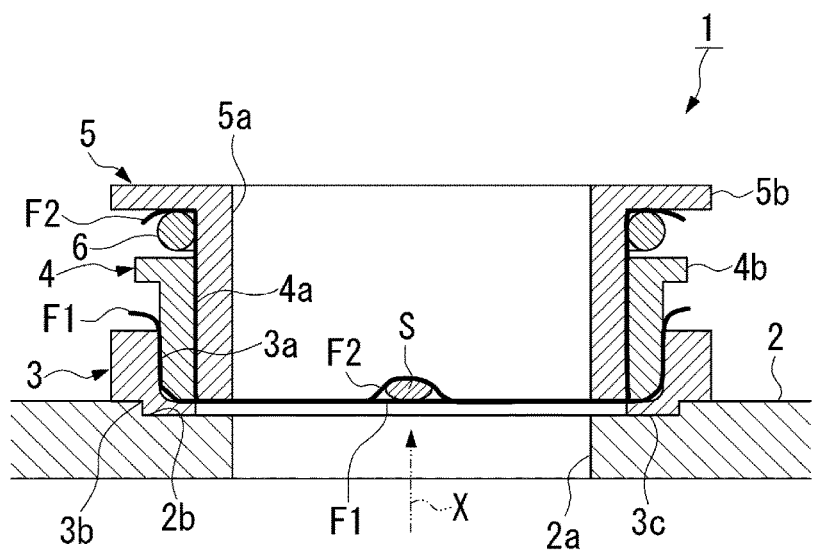
FIG. 1 is a cross-sectional view showing a state of being placed on a holder mounting portion of an X-ray analyzer, in an embodiment of a sample holder for X-ray analysis according to an embodiment of the present invention.
Figure 2:
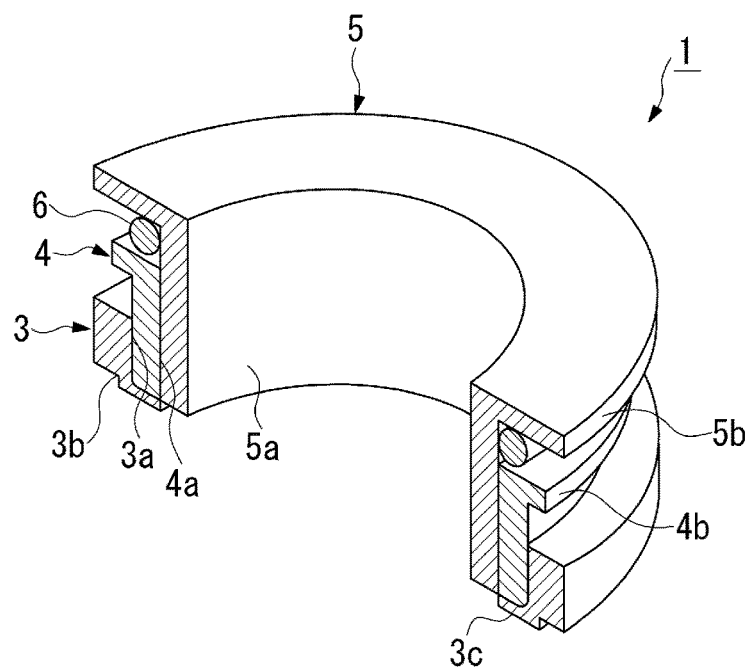
FIG. 2 is a perspective view showing the sample holder for X-ray analysis (except for a film) when having been broken into half, in the embodiment.
Figure 3:
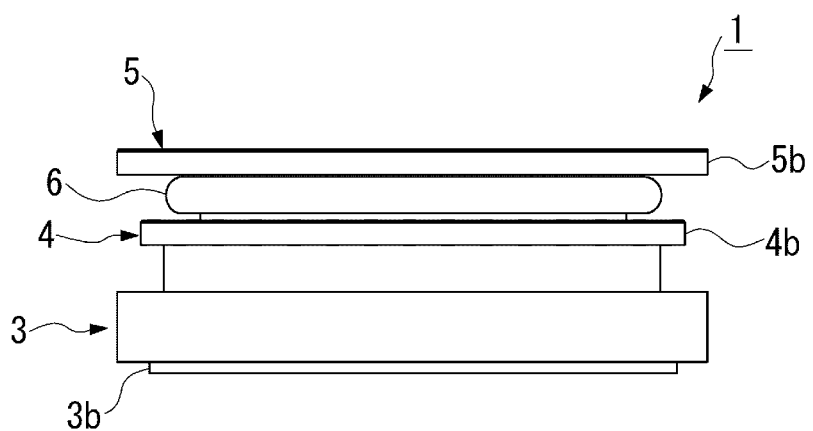
FIG. 3 is a front view showing the sample holder for X-ray analysis (except for a film) in the embodiment.
Figure 4:
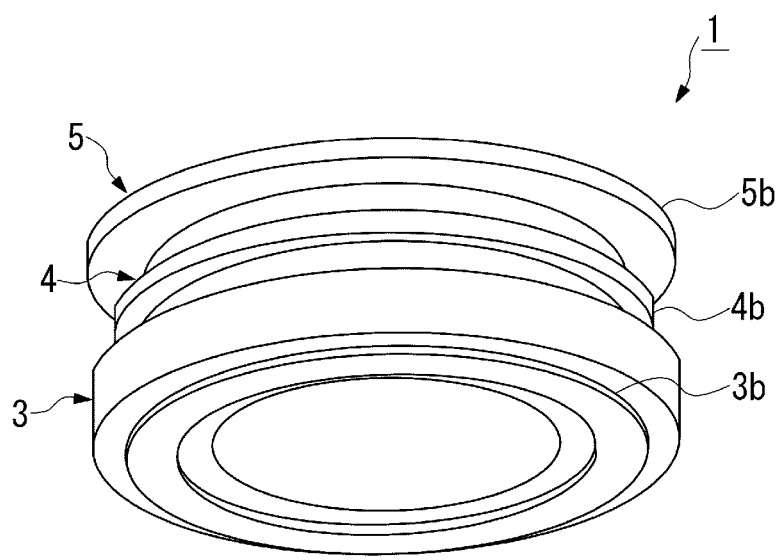
FIG. 4 is a perspective view as viewed from below showing the sample holder for X-ray analysis (except for a film and an elastic ring) in the embodiment.

Hereinafter, a sample holder for X-ray analysis and a jig for sample installation according to an embodiment of the present invention will be described with reference to the accompanied drawings.

A sample holder 1 for X-ray analysis of the embodiment is a sample holder for holding a sample for an X-ray analyzer such as an X-ray fluorescence spectrometer. The sample holder 1 is installed in a holder mounting portion 2 which is a sample base, and is provided with a first annular member 3, a second annular member 4 which is inserted into and fitted into the first annular member 3 in a state where a first film F1 is sandwiched between itself and the first annular member 3 and in which the first film F1 is provided to be stretched so as to cover a lower opening portion, and a third annular member 5 which is inserted into and fitted into the second annular member 4 in a state where a second film F2 is sandwiched between itself and the second annular member 4 and in which the second film F2 is provided to be stretched so as to cover a lower opening portion, as shown in FIGS. 1 to 4.

The first film F1 is sandwiched between an inner peripheral surface 3a of the first annular member 3 and an outer peripheral surface of the second annular member 4 and provided to be stretched at the lower opening portion, and the second film F2 is sandwiched between an inner peripheral surface 4a of the second annular member 4 and an outer peripheral surface of the third annular member 5 and provided to be stretched at the lower opening portion.

Therefore, the sample holder 1 for X-ray analysis sandwiches a sample S for X-ray analysis between the first film F1 and the second film F2 each provided to be stretched at the lower opening portion of each of the second annular member 4 and the third annular member 5.

The first annular member 3, the second annular member 4, and the third annular member 5 are cylindrical members each formed of resin or the like and having different heights.

The second annular member 4 is formed to be higher than the first annular member 3, and the third annular member 5 is formed to be higher than the second annular member 4.

In the first annular member 3, a bottom support portion 3c protruding radially inward and formed over the entire circumstance of the lower opening portion is formed at a lower portion. A lower end of the second annular member 4 is supported on the upper surface of the bottom support portion 3c in a state where the first film F1 is sandwiched therebetween.

Further, the sample holder 1 for X-ray analysis is provided with an elastic ring 6 which is mounted above the second annular member 4 and on the outer peripheral surface of the third annular member 5 in a state of sandwiching an outer peripheral edge portion of the second film F2 therebetween and thus fixes the second film F2.

The elastic ring 6 is, for example, configured by a rubber band.

Further, as the first film F1 and the second film F2, for example, a resin film such as a polyester film which is called a Mylar (registered trademark) film can be adopted, and a thin film with a thickness of several microns, which is transparent and in which impurities do not come out, is preferable.

A stepped portion 3b having a cutout shape is formed in an outer periphery of the lower portion of the first annular member 3.

In the second annular member 4, a first flange portion 4b protruding radially outward, thereby having an expanded diameter, is formed at an upper portion, and also in the third annular member 5, a second flange portion 5b protruding radially outward, thereby having an expanded diameter, is formed at an upper portion. That is, the elastic ring 6 is provided between the first flange portion 4b and the second flange portion 5b.

Figure 5:
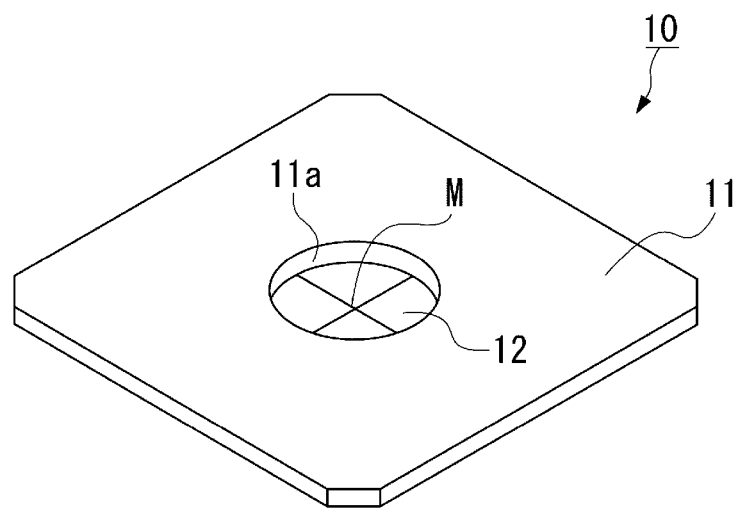
FIG. 5 is a perspective view showing an embodiment of a jig for sample installation according to an embodiment of the present invention.
Figure 6:
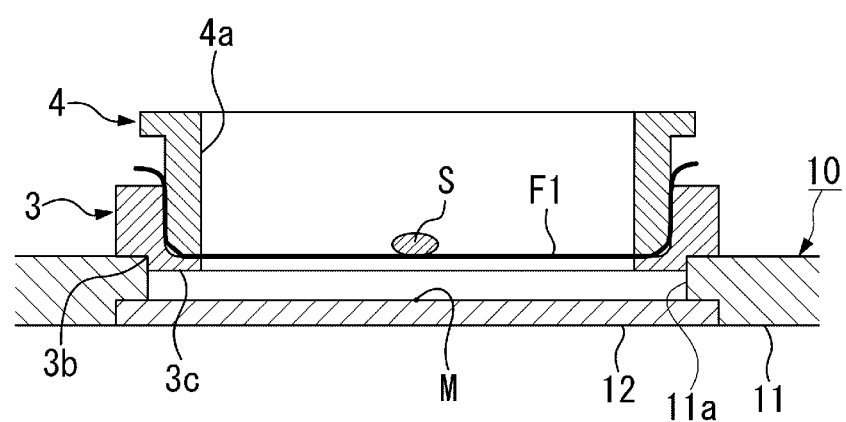
FIG. 6 is a cross-sectional view for describing a process of setting a sample in the sample holder for X-ray analysis by using the jig for sample installation in the embodiment.

A jig 10 for sample installation is configured as a jig which is used when installing the sample S for X-ray analysis in the sample holder 1 for X-ray analysis, and is provided with a plate-shaped jig main body 11 having an installation hole 11a into which the lower portion of at least the first annular member 3 can be fitted, and a transparent plate portion 12 provided to cover a lower opening portion of the installation hole 11a, as shown in FIGS. 5 and 6.

The transparent plate portion 12 is a transparent glass plate or a transparent plastic plate, and a mark M indicating the center of the installation hole 11a is formed on the surface. The mark M is, for example, configured by an intersection point of cross lines or the like drawn on the surface of the transparent plate portion 12.

The installation hole 11a is regarded as an inner diameter corresponding to the diameter of the stepped portion 3b of the first annular member 3 and is set in a circular shape into which the bottom support portion 3c can be fitted.

Next, a method of setting the sample S in the sample holder 1 for X-ray analysis by using the jig 10 for sample installation will be described with reference to FIG. 6.

First, as shown in FIG. 6, the lower portion (the bottom support portion 3c) of the first annular member 3 is fitted into the installation hole 11a of the jig 10 for sample installation. In this case, a state is created in which the stepped portion 3b of the lower portion is locked to an outer peripheral end of an upper portion of the installation hole 11a and the bottom support portion 3c is inserted into the installation hole 11a, and thus the first annular member 3 is positioned.

Next, the first annular member 3 is covered with the first film F1, and the second annular member 4 is pushed into the first annular member 3 from above the first film F1 and the first film F1 is pushed into the first annular member 3. Accordingly, the first film F1 is provided to be stretched so as to cover the lower opening portion of the second annular member 4. At this time, a lower end of the second annular member 4 is supported by being brought into contact with the bottom support portion 3c of the first annular member 3.

In this state, the sample S is placed on the first film F1 provided to be stretched at the lower opening portion of the second annular member 4. At this time, since the mark M of the transparent plate portion 12 can be visually recognized through the first film F1, the sample S is placed at the center of the installation hole 11a with the mark M as a reference.

On the other hand, the lower opening portion of the third annular member 5 is covered with the second film F2, and a peripheral edge portion of the second film F2 is fixed to the outer peripheral surface of the third annular member 5 by the elastic ring 6. At this time, the second film F2 is fixed with tension looser than that of the first film F1 provided to be stretched.

Next, after the sample S is placed, the third annular member 5 with the second film F2 fixed thereto is pushed into the second annular member 4 from above. At this time, the position of the sample S is fixed by sandwiching the sample S between the first film F1 and the second film F2, whereby the sample S is set in the sample holder 1 for X-ray analysis.

In the embodiment, fixing is performed by the elastic ring 6 with the tension of the second film F2 made weaker than that of the first film F1, and therefore, it may become possible to nip the sample S in such a manner that the second film F2 becomes convex into the third annular member 5 with the first film F1 provided to be stretched flatly. Accordingly, it may become possible to hold the sample S without sagging the first film F1, and thus it is possible to maintain the position of the first film F1 which becomes a reference plane determining the distance between the sample S and an X-ray tube.

When the sample holder 1 for X-ray analysis with the sample S set therein in this way is mounted on the X-ray analyzer, the sample holder 1 for X-ray analysis with the sample S set therein is mounted on a hole for a holder 2a formed in the holder mounting portion 2 which is a sample base, as shown in FIG. 1, and is put in the X-ray analyzer along with the holder mounting portion 2. Incidentally, a concave portion 2b having a stepped portion shape, to which the stepped portion 3b is locked, whereby the lower portion of the first annular member 3 can be fitted therein, is provided in an outer edge of an upper portion of the hole for a holder 2a of the holder mounting portion 2, and thus the sample holder 1 for X-ray analysis is positioned simply by being installed in the hole for a holder 2a.

The sample S set in the X-ray analyzer in this manner is irradiated with primary X-rays X through the first film F1 from below the hole for a holder 2a during X-ray analysis.

Figure 7:
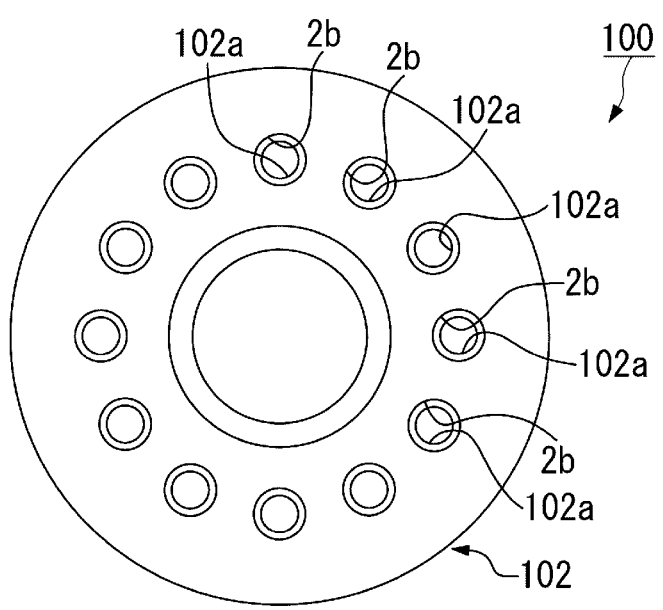
FIG. 7 is a plan view showing a sample changer of the X-ray analyzer in the embodiment.

In a case of analyzing and measuring a plurality of sample holders 1 for X-ray analysis, a sample changer (a holder mounting section) 100 on which the plurality of sample holders 1 for X-ray analysis can be mounted is used, as shown in FIG. 7. That is, the respective sample holders 1 for X-ray analysis are mounted on a plurality of holes for a holder 102a formed in the sample changer 100.

In this manner, in the sample holder 1 for X-ray analysis of the embodiment, the sample S is sandwiched between the first film F1 and the second film F2 each provided to be stretched at the lower opening portion of each of the second annular member 4 and the third annular member 5. Therefore, the sample S may be prevented from being shifted when sandwiched between a pair of films, and since the films are thin, it may cause less affect for X-ray measurement and accurate measurement becomes possible. Further, the position of the first film F1 is set at the optimum position of the distance between the sample S and the X-ray tube, whereby it is possible to make the distance between the sample S and the X-ray tube always constant. In addition, the sample S is sandwiched between a pair of films, and therefore, limitations on the size or the shape of the sample S are few, and thus it becomes possible to set a variety of samples S.

Further, since the sample holder 1 for X-ray analysis is provided with the elastic ring 6 which is mounted above the second annular member 4 and on the outer peripheral surface of the third annular member 5 in a state of sandwiching the outer peripheral edge portion of the second film F2 therebetween and thus fixes the second film F2, it is possible to adjust the degree of the tension of the second film F2 by the elastic ring 6.

In addition, the stepped portion 3b having a cutout shape is formed in the outer periphery of the lower portion of the first annular member 3, and therefore, by providing the concave portion 2b having a stepped portion shape, to which the stepped portion 3b is locked, whereby the lower portion of the first annular member 3 can be fitted therein, in the holder mounting portion 2 of the X-ray analyzer, it is possible to perform positioning with an X-ray irradiation port, and it becomes easy to match the sample S to a target position, and thus it also becomes possible to dispose the sample S at the same position again.

In the jig 10 for sample installation, the mark M indicating the center of the installation hole 11a is formed on the transparent plate portion 12, and therefore, it may become possible to place the sample S on the first film F1 with the mark M of the transparent plate portion 12 visible through the first film F1 as a reference, in a state where the first annular member 3 and the second annular member 4 with the first film F1 provided to be stretched therebetween are fitted into the installation hole 11a. Therefore, due to using the jig 10 for sample installation, it becomes easy to set the sample S at a measurement position corresponding to the center of an X-ray beam on the outside of the X-ray analyzer.

According to the embodiment, it may become possible to accurately set samples of various shapes at a position where it is desired to perform the irradiation with X-rays, on the inside or the outside of the X-ray analyzer, and it is possible to prevent the held sample S from being shifted due to vibration or the like.

Incidentally, the technical scope of the present invention is not limited to the embodiment described above, and it is possible to apply various changes within a scope which does not depart from the gist of the present invention.

For example, in the embodiment described above, the first to third annular members are set to be cylindrical members. However, a tubular member such as an elliptic tubular member or a rectangular tubular member is also acceptable.

In the embodiment described above, the mark provided in the transparent plate portion is configures as a crosshair. However, as long as a target installation position of a mark can be visually recognized, other types and shapes of marks are also acceptable. For example, a small circular mark or the like is also acceptable as the mark provided in the transparent plate.

What is claimed is:

1. A sample holder for X-ray analysis comprising:
a first annular member;
a second annular member configured to be inserted and fitted into the first annular member in a state where a first film is sandwiched between the first annular member and the second annular member while the first film is being stretched to cover a lower opening portion of the second annular member; and
a third annular member configured to be inserted and fitted into the second annular member in a state where a second film is sandwiched between the second annular member and the third annular member while the second film is being stretched to cover a lower opening portion of the third annular member,
wherein the first film being stretched to cover the lower opening portion of the second annular member and the second film being stretched to cover the lower opening portion of the third annular member are configured to hold a sample for X-ray analysis by sandwiching the sample between the first film and the second film, wherein the third annular member is configured to have a height higher than that of the second annular member, and wherein the sample holder further comprises:

an elastic ring configured to be mounted above the second annular member and on an outer peripheral surface of the third annular member in a state where an outer peripheral edge portion of the second film is sandwiched between the elastic ring and the outer peripheral surface of the third annular member to attach the second film to the third annular member.

2. The sample holder according to claim 1, wherein the first annular member is provided with a stepped portion having a cutout shape in an outer periphery of a lower portion of the first annular member.

3. A jig for installing a sample in the sample holder for X-ray analysis according to claim 1, the jig comprising:

a plate-shaped jig main body having an installation hole into which a lower portion of at least the first annular member is fitted; and a transparent plate portion provided to cover a lower opening portion of the installation hole, wherein the transparent plate portion is provided with a mark indicating the center of the installation hole.

* * * * *